United States Patent [19]

Rudd et al.

[11] 4,138,457

[45] Feb. 6, 1979

[54] METHOD OF MAKING A PLASTIC TUBE WITH PLURAL LUMENS

[75] Inventors: Ralph E. Rudd, Granville; John I. Huggins, Argyle, both of N.Y.

[73] Assignee: Sherwood Medical Industries Inc., St. Louis, Mo.

[21] Appl. No.: 714,230

[22] Filed: Aug. 13, 1976

[51] Int. Cl.² .................... B29C 17/02; B29D 23/04
[52] U.S. Cl. ............................ 264/500; 264/530; 264/167; 264/541; 264/173; 264/177 R; 264/209; 425/326.1; 425/381
[58] Field of Search .............. 264/89, 90, 95, 99, 264/100, 40.3, 40.5, 167, 173, 177 R, 209; 425/326 R, 380, 381, 326.1

[56] References Cited

U.S. PATENT DOCUMENTS

| | | | |
|---|---|---|---|
| 3,002,615 | 10/1961 | Lemelson | 425/381 X |
| 3,304,353 | 2/1967 | Haratuneian | 264/100 X |
| 3,674,404 | 7/1972 | Burus et al. | 425/326 R |
| 3,755,525 | 8/1973 | Sheridan et al. | 264/209 X |
| 3,929,951 | 12/1975 | Shibata et al. | 264/209 X |

FOREIGN PATENT DOCUMENTS

| | | | |
|---|---|---|---|
| 38-4186 | 4/1963 | Japan | 264/167 |
| 740407 | 11/1955 | United Kingdom | 425/381 |
| 1130598 | 10/1968 | United Kingdom | 264/177 R |

*Primary Examiner*—Jan H. Silbaugh
*Attorney, Agent, or Firm*—S. N. Garber; W. R. O'Meara

[57] ABSTRACT

A plastic tube is provided which has a main lumen, an auxiliary lumen, and an integral connector at one end for connecting the main lumen in fluid communication with another device. The auxiliary lumen extends longitudinally within the side wall of the tube with the integral tube connector free of the auxiliary lumen. The tube can be made by extruding thermoplastic material through a die having a hollow main lumen die pin and a hollow auxiliary lumen die pin adjacent the die outlet orifice. Air under pressure is supplied to both die pins to produce tubing extrudate having main and auxiliary lumens. The pressure of the air supplied to the auxiliary lumen forming pin is reduced at programmed intervals during the extrusion of the tubing so that selected portions are free of an auxiliary lumen or have a lumen of limited size. The tubing can be severed so that it has a selected portion at one end that can serve as an end connector.

18 Claims, 12 Drawing Figures

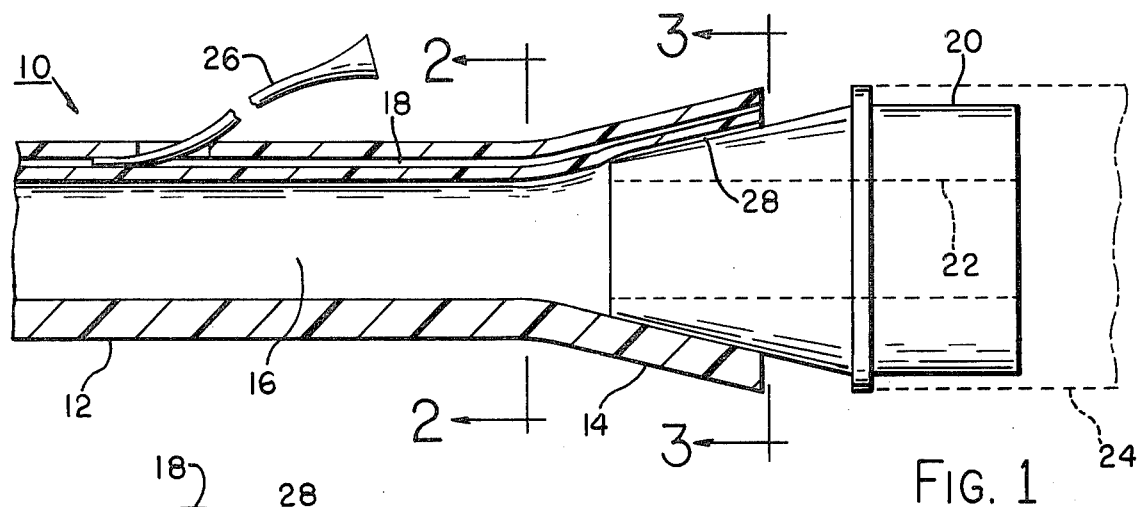
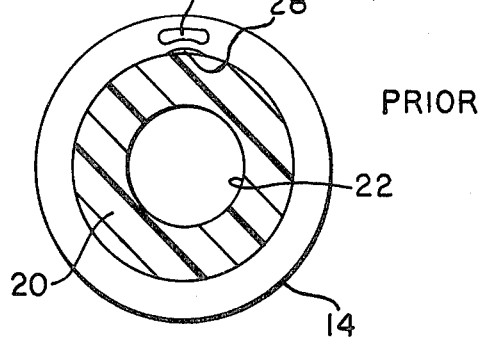 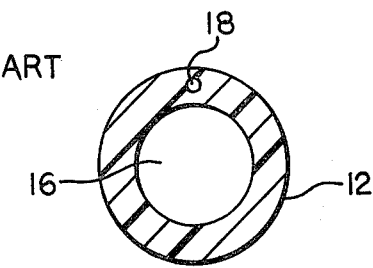
PRIOR ART
FIG. 3    FIG. 2
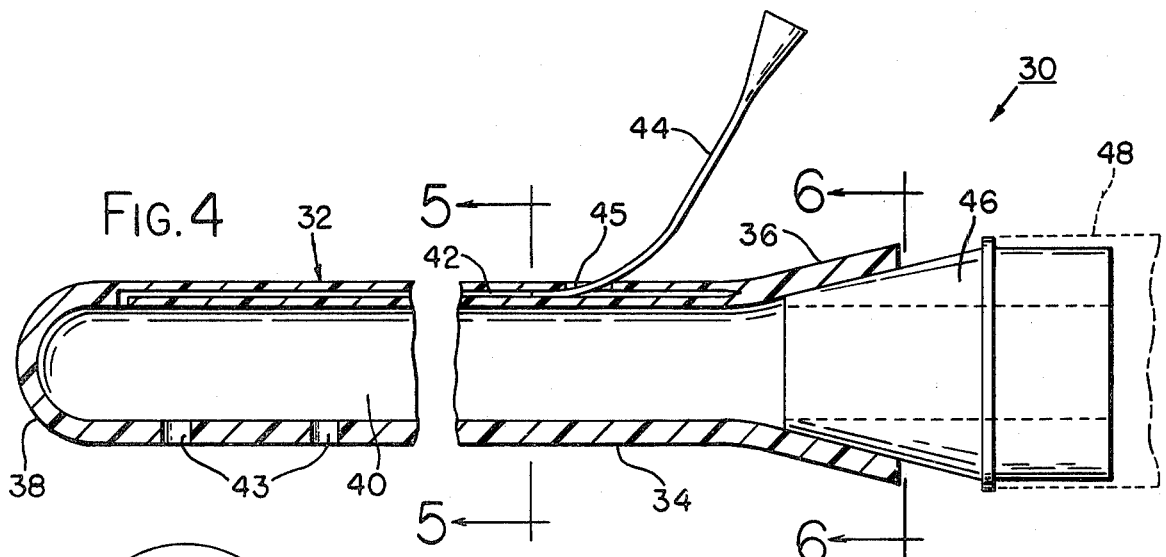
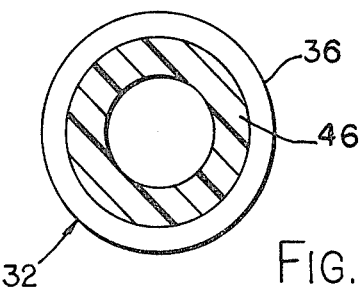 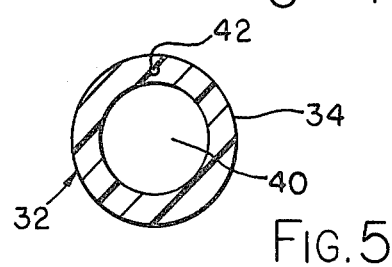
FIG. 6    FIG. 5

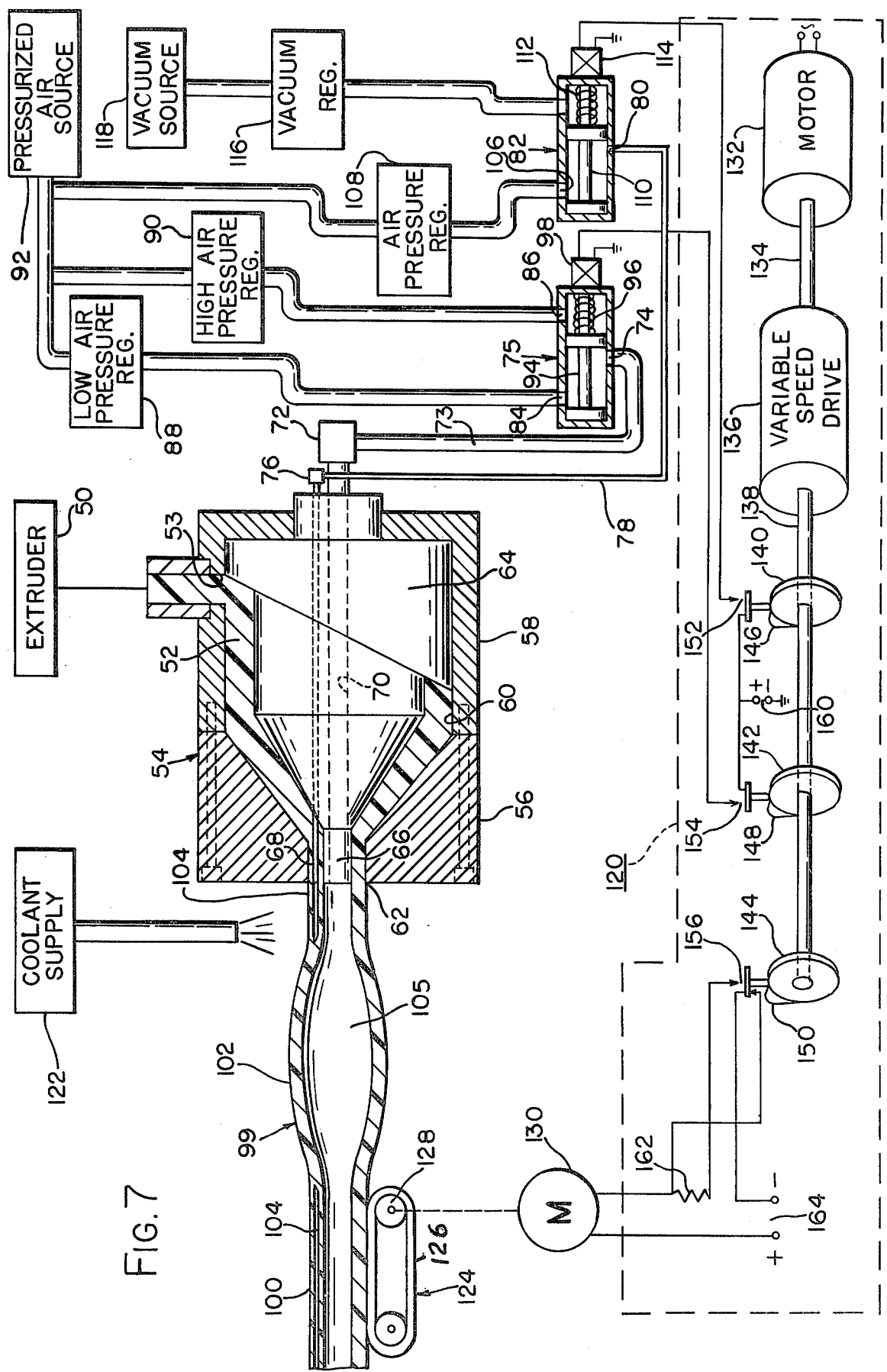

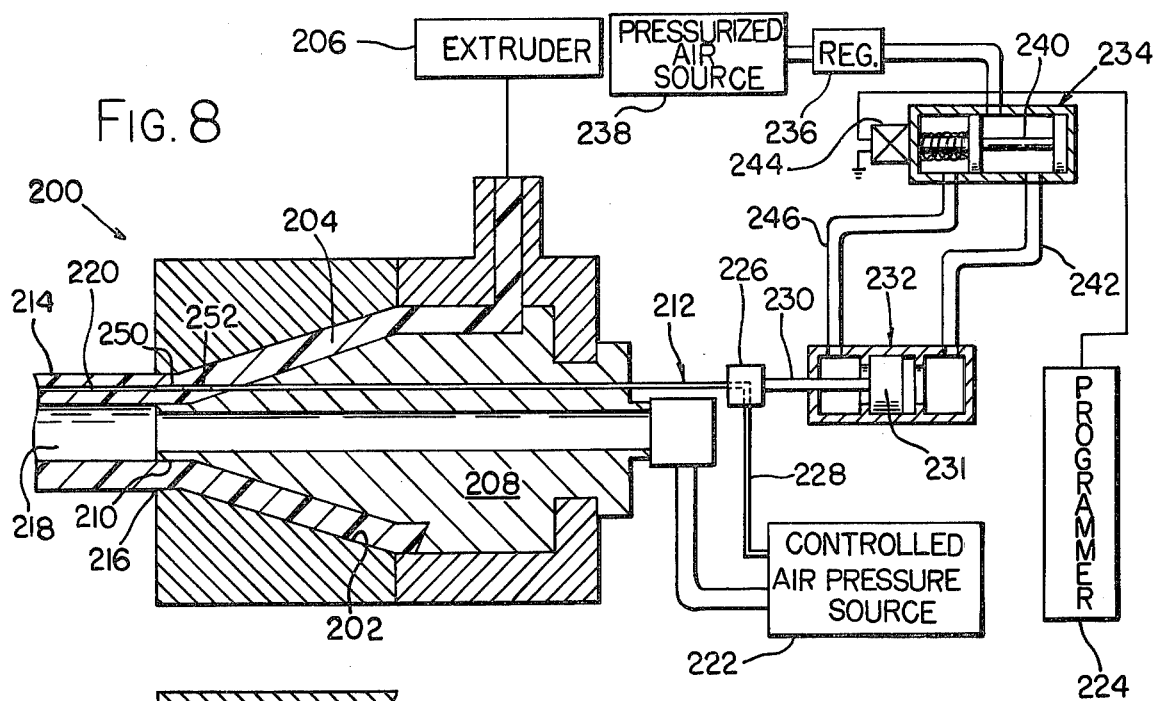
FIG. 8
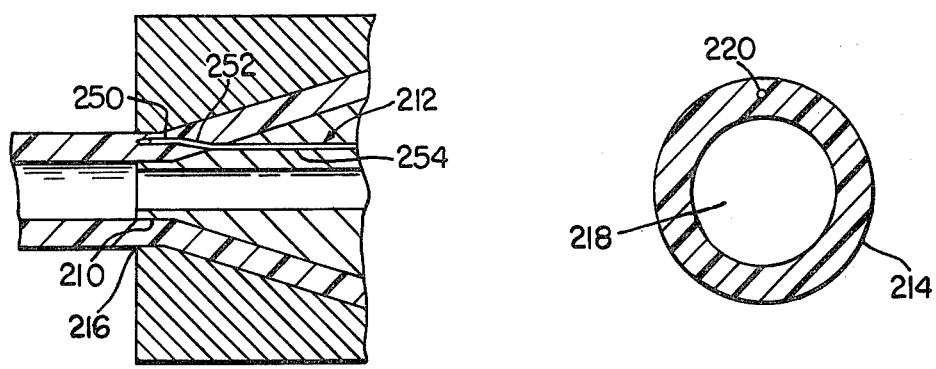
FIG. 11
FIG. 9
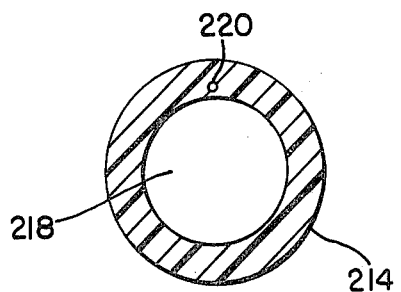
FIG. 10
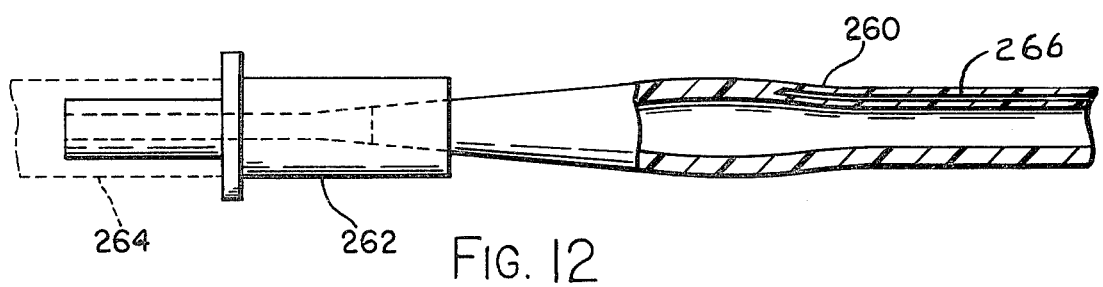
FIG. 12

METHOD OF MAKING A PLASTIC TUBE WITH PLURAL LUMENS

BACKGROUND OF THE INVENTION

Many types of plastic tubes such as medical tubes and catheters are provided with one or more auxiliary lumens. For example, some suction catheters for draining or irrigating body cavities have an integral connector at the proximal end for connecting the main lumen with a suction force, and a distal end having openings extending through the tube side wall for communicating with body cavity fluids. An auxiliary lumen extending longitudinally within the side wall of the tube may be used to supply gas, such as air, or a liquid, such as an irrigation liquid, to the distal end of the main lumen or body cavity. Auxiliary lumens are also used in catheters to convey x-ray opaque liquid to a body cavity during fluroscopy. Also, metal rods can be disposed in an auxiliary lumen so that the catheter can be bent or formed into a desired permanent configuration such as to facilitate insertion of the catheter into a body cavity.

Plastic tubes with auxiliary lumens are conventionally made by extruding thermoplastic material through a suitable forming die to produce tubing with an auxiliary lumen. The extrudate is severed at selected points to provide a tube of desired length. One end portion of the tube may serve as an integral connector for coupling the tube with another device, such as a source of vacuum or other fluid system. The tubing extrudate may be produced with an enlargement or tapering "bubble" which, when cut through to form the tube, provides a conical or tapering integral tube connector. A rigid fluid connector or coupling element may be inserted into or over the tube connector (depending on the type) and rotated a limited amount into tight frictional engagement with the tube connector.

A serious drawback in the use of such tubes, especially when employed as medical tubes or catheters, is that a fluid leak sometimes occurs between the mating surfaces of the integral tube connector and the coupling element in an area adjacent the auxiliary lumen. Such fluid leaks occur because the wall of the tube connector adjacent the auxiliary lumen is generally thinner and more flexible than the other portions of the tube connector. Thus, sometimes fluid leaks from the main lumen at the connection of the tube and coupling element.

Auxiliary lumens can be closed after the extrudate has been cut into tubes or desired lengths by inserting filling material into the lumens. However, such a method generally increases the labor time and cost.

SUMMARY OF THE INVENTION

Accordingly, it is an object of the present invention to provide an improved plastic tube having main and auxiliary lumens which avoids the above undesirable features.

Another object is to provide a novel economical method of making a plastic tube having main and auxiliary lumens which is capable of making a good fluid connection with another device without the danger of fluid leakage at the connection.

Another object is to provide a novel plastic tube and economical method of making the tube wherein the tube has predetermined portions with and without an auxiliary lumen.

In accordance with one aspect of the present invention, a plastic tube is provided which has main and auxiliary lumens but with an end portion which is adapted for connection with another device substantially free of the auxiliary lumen or one of limited size. In accordance with another aspect of the invention, a method for making a plastic tube having main and auxiliary lumens includes extruding plastic tubing through a die having main and auxiliary lumen forming members, applying fluid pressure to the auxiliary lumen forming member to provide fluid pressure at the end thereof for producing an auxiliary lumen in a predetermined portion of the extrudate, reducing the pressure at the end of the auxiliary lumen at programmed intervals during the extrusion of other predetermined portions, and severing the tubing so as to provide a tube which includes a predetermined portion having an auxiliary lumen and at least one of the other predetermined portions.

These as well as other objects and advantages of the present invention will become apparent from the following detailed description and drawings.

BRIEF DESCRIPTION OF THE DRAWINGS

FIG. 1 is a fragmentary, longitudinal cross-sectional side view of a plastic tube of the prior art;

FIG. 2 is a cross-sectional view taken along the lone 2—2 of FIG. 1;

FIG. 3 is a cross-sectional view taken along the line 3—3 of FIG. 1;

FIG. 4 is a longitudinal cross-sectional view of a catheter made in accordance with the present invention;

FIG. 5 is a cross-sectional view taken along line 5—5 of FIG. 4;

FIG. 6 is a cross-sectional view taken along line 6—6 of FIG. 4;

FIG. 7 is a schematic view illustrating a method and apparatus for making plastic tubing used in producing the catheter of FIG. 4;

FIG. 8 is a schematic view illustrating a modified method and apparatus for making plastic tubing used in producing tubes in accordance with the present invention;

FIG. 9 is a cross-sectional view of tubing capable of being produced by the apparatus of FIG. 8;

FIG. 10 is a cross-sectional view of tubing capable of being produced by the apparatus of FIG. 8;

FIG. 11 is a fragmentary view of the apparatus of FIG. 8 illustrating the auxiliary lumen forming member retracted to eliminate the auxiliary lumen in a predetermined portion of the tubing; and FIG. 12 is a fragmentary elevational view of tubing capable of being made by the apparatus of FIGS. 7 or 8 and a fluid coupling element connected thereto.

DESCRIPTION OF THE PREFERRED EMBODIMENT

Referring now to the drawings, and particularly to FIGS. 1-3, a plastic tube of the prior art is shown in the form of a medical tube or catheter indicated generally at 10. The catheter 10 includes a main straight tube portion 12 integral with a connector portion 14 which tapers radially outwardly toward the right or proximal end of the tube. The tube 10 has a main lumen 16 and a longitudinally extending auxiliary lumen 18 within the side wall of the tube. A fluid connector or coupling element 20 having a lumen 22 connects the main lumen 16 in fluid communication with another device such as another tube indicated in phantom at 24. The tube 10 and coupling element 20 are connected together by urging them toward each other while effecting limited relative rotation. A tube 26 is shown connected in fluid communication with auxiliary lumen 18 for passing a gas or liquid into the lumen 18.

As previously mentioned, a fluid leakage path sometimes occurs between the integral connector portion of the tube and the coupling element. Such a leakage path is shown in exaggeration at 28 in FIGS. 1 and 3. This leakage path is due to the relatively thin flexible wall between the lumens 16 and 18 which, when fluid pressure exists in lumen 16, has a greater tendency to move away from the adjacent surface of the coupling element 20 than the other thicker wall portions of the integral tube connector 14.

One well known method of forming bubbles is to reduce the "take-off speed", that is, the speed at which the extrudate is drawn from the die while increasing air pressure applied to the main lumen forming member or pin. The take-off speed is reduced to maintain the wall thickness at a desired dimension in the bubble. Reduction in the withdrawal speed increases die swell which tends to make the auxiliary lumen larger. The enlarged auxiliary lumen in the bubble increases the chances of fluid leakage when a fluid coupling element is used.

In FIGS. 4-6 there is shown a catheter 30 made in accordance with the present invention which overcomes this problem. The catheter 30, which is shown in the form of a suction catheter, includes a tube 32 having a straight or main portion 34 of constant diameter with a radially outwardly extending integral connector portion 36 at the proximal end, and a closed distal end 38. Catheter 30 has a main lumen 40 and an auxiliary lumen 42 extending within the side walls of the tube 32 and which is open to the main lumen 40 near the distal end of the tube. A tube 44 is connected with the auxiliary lumen to supply fluid to the main lumen at a point near the distal end of the tube. A small opening 45 is provided in the side wall of the tube 32, and the tube 44 inserted through the opening 45 and into the auxiliary lumen 42, the tube being secured in place such as by cement or the like. The tube 32 has a plurality of openings 43 extending through the side wall at the distal end for drawing fluids into the main lumen when a suction force is applied to the main lumen such as by means of a connector 46 connected to a suction tube 48 which, in turn, may be connected to a suction source. In such a case, air may flow into tube 44 and into the main lumen 40 to prevent body tissue from being drawn into the opening 43.

As seen in FIGS. 4 and 6, the integral tube connector portion 36 does not have an auxiliary lumen but rather a solid wall of substantially constant thickness and formed entirely of the extrudate material. Thus, the connector 46 may be tightly fitted into tube connector 36 without the danger of fluid leaking from the main lumen between the connector 36 and the coupling element 46.

FIG. 7 illustrates a method and apparatus for producing plastic tubing from which tubes, such as tube 32 of FIG. 4, can be economically made. The apparatus includes a suitable well-known or conventional extruder 50 for supplying a melt or molten thermoplastic material 52, such as polyvinyl chloride, to an inlet 53 of a tube forming die 54.

The die 54 has a sizing bushing 56 connected by bolts to a die body 58 and which provides a die cavity 60 for receiving the melt 52. The die cavity 60 has a die outlet or orifice 62. Disposed in the cavity 60 is a forming member 64 having a main lumen forming member or pin 66 extruding to the die orifice 62, and an auxiliary lumen forming member or pin 68 also extending to the die orifice 62. The main lumen forming pin 66 has a bore 70 extending through member 64 to a fluid connector 72 which is, in turn, connected by a conduit 73 to an outlet 74 of a slide or piston valve 75. The auxiliary lumen forming pin 68 is in the form of a tubular member extending through the member 64 and has its bore connected in fluid communication with a fluid connector 76 connected to a conduit 78 which is connected to an outlet 80 of a slide or piston valve 82. Valve 75 has a pair of air pressure inlets 84 and 86 connected respectively to the outlets of air pressure regulators 88 and 90 which are supplied air from an air pressurized source 92.

Valve 75 has a piston 94 disposed in the cylinder of the valve which is slidable between two positions. Piston 94 is biased to one position, such as the position shown in the drawing, by a spring 96 connected to the rod of the piston. In the position shown in FIG. 7, valve 75 connects the outlet side of pressure regulator 88 to the valve outlet 74 and the main lumen forming pin 66. The valve 75 is provided with an actuating relay coil 98 coupled to the piston rod which, when energized, moves the piston 94 rightwardly against the force of spring 96 to close the inlet 84 from the outlet 74, and open the inlet 86 to the outlet 74 to thereby connect the pressure outlet from pressure regulator 90 to the main lumen forming pin 66. The pressure regulator 88 supplies a substantially constant relatively low pressure compared to that supplied to the valve 75 by the pressure regulator 90. As will be further explained hereinafter, during the extrusion of plastic tubing when the pressure regulator 88 supplied relatively low air pressure to the main lumen pin 66, the extrudate indicated at 99 has a constant or smaller diametered portion 100, and when the pressure regulator 90 is supplying relatively high pressure to the main lumen pin 66, an enlargement or tapering bubble 102 is extruded from the die 54. The extrudate 99 has an auxiliary lumen 104 and a main lumen 105.

The valve 82, which controls the air or gas pressure applied to the melt 52 at the end of the auxiliary lumen pin 68, has an inlet 106 connected to the outlet of an air pressure regulator 108 having its inlet connected to the pressurized air source 92. The pressure outlet of the regulator 108 applies a predetermined positive air pressure to the pin 68 for producing a desired auxiliary lumen 104. Valve 82 has a piston 110 which is biased by a spring 112 to the position shown in FIG. 7. It also has a solenoid coil 114 which, when energized, moves the piston 110 to the right to close off the air pressure regulator 108 from the outlet 80 and auxiliary lumen forming pin 68, and connects the outlet side of a vacuum regulator 116 to the outlet 80. The regulator 116 is a vacuum regulator having its inlet connected to a vacuum source 118. When the valve 82 is actuated to apply the vacuum for regulator 116 to the auxiliary lumen forming pin 68, a negative pressure is applied to the extrudate at the end of pin 68 to eliminate the formation of the auxiliary lumen 104, that is, the lumen is substantially entirely eliminated in the desired predetermined portions of the extrudate. As seen in the drawing, the bubble 102 is free of any auxiliary lumen but an auxiliary lumen is formed in the portions 100 of the extrudate on both sides of the bubble. The solenoid coils 98 and 114 of relay valves 75 and 82 are controlled by a programmer indicated generally at 120.

As the molten plastic extrudate emerges from the die orifice 62, it is cooled by coolant supply generally indicated at 122 to effect solidification of the tubing material. Also, a take-off drive 124 withdraws the solidified tubing at a desired rate, the rate of withdrawal of the extrudate being correlated with the air pressures applied to produce a bubble having a desired wall thickness, for example, the walls of the bubble may be the same as the walls of the straight portions 100. The tube withdrawal mechanism 124 is shown including an endless belt 126 rotated by a drive wheel 128 and which engages the bottom side of the solidified tubing. Drive wheel 128 is driven by a DC motor 130, the speed of which is also controlled by the programmer 120.

The programmer 120 may be an electronic type programmer which includes electronic timing circuits and which synchronizes and correlates the operation of the valves 75 and 82 and the take-off motor 130 to continuously produce an extrudate having repetitive configurations such as substantially constant portions and predeterminately located enlarged portions or bubbles. The programmer 120 is shown as a motor driven mechanical arrangement of cams and includes an electric motor 132 driving a shaft 134 which, in turn, drives a variable speed drive mechanism 136 having an output shaft 138. Shaft 138 rotates three cams 140, 142 and 144 that are affixed to the shaft 138. Cam members 140 and 142 respectively control the actuation of relays 82 and 75 while the cam member 144 controls the speed of motor 130 to control the speed at which the extrudate is withdrawn from the die. The cam members 140, 142 and 144 are shown as circular discs having camming surfaces 146, 148 and 150, respectively, for operating cam operated switches 152, 154 and 156, respectively. When the camming surfaces of the camming members engage and actuate the camming switches, the solenoid coils 98 and 114 are energized to actuate the valves 75 and 82 and reduce the speed of the take-off motor 130. Switches 152 and 154, when actuated, connect a relay coil voltage source 160 to the coils 98 and 112. The switch 156, when actuated by the camming surface 150, connects a resistor 162 in series with the motor 130 and the motor power supply source 164 to reduce the speed of the motor 130. In the illustrated embodiment, the controls for the valves 75 and 82 and the motor 130 are shown to be actuated about the same time by the cams fixed to the common shaft 138. However, as is well known, control of the air pressure supply to the lumen forming pins and the speed of take-off of the extrudate can be timed to obtain various tubular configurations and effects. The programmer 120 may be of the electronic type having electronic timers and correlating circuits for synchronously controlling the air pressures applied to the forming pins and signals for controlling the speed of the extrudate take-off drive.

In operation, the extruder 50 continuously supplies melt, such as molten polyvinyl chloride 52, to the die 54 which flows out of the die orifice 62 as extrudate 99. When the cam members 140, 142 and 144 are in the positions shown, the three cam switches 152, 154 and 156 are open. At this time, valve 75 supplies the relatively low air pressure to the main lumen forming pin 66, and the valve 82 supplies positive pressure to auxiliary lumen forming pin 68. Also, the resistor 162 is by-passed so that motor 130 drives the take-off drive 124 at a relatively high rate. Under these conditions, the extrudate produced is a straight portion 100 having a constant diameter with both auxiliary and main lumens 104 and 105.

When the camming surfaces 146, 148 and 150 of the cams actuate the three switches 152, 154 and 156, the solenoid coils 98 and 114 are energized to actuate valves 75 and 82, and the resistor 162 is inserted into the supply circuit for motor 130 to reduce its speed. Under these conditions, relatively high air pressure from regulator 90 is supplied by valve 75 to forming pin 66, a vacuum is applied from vacuum regulator 116 to forming pin 68 by valve 82, and the take-off drive speed is reduced. The inner and outer diameters of the extrudate 99 increase, and the auxiliary lumen 104 terminates due to the reduction in air pressure at the end of the pin 68 as a result of the vacuum applied from valve 82. The leading portion of bubble 102 is thus formed. As the camming surfaces move by the switches, the switches return to their open positions shown. The take-off speed now increases, the air supplied to the main lumen forming pin 66 decreases since the air supplied to it again now comes from regulator 88, and the auxiliary lumen forming pin is again supplied positive pressure air from regulator 108 through valve 82. The increased withdrawal rate of the extrudate and decrease in air supplied to pin 66 cause the inner and outer diameters of the extrudate to decrease from their maximum values to produce the trailing end portion of bubble 102. The return of positive pressure to forming pin 68 causes the auxiliary lumen 104 to again be produced in the extrudate. As seen in FIG. 7, extrudate 99 has a relatively small auxiliary lumen 104 on both sides of bubble 102, the bubble being free of the auxiliary lumen. As the shaft 138 continues to rotate, the switches, of course, continue to operate to produce straight portions 100, and bubbles 102 at predetermined locations along the extrudate.

The switches 152, 154 and 156 are operated in response to the rotation of shaft 138, and the timing or sequence of operation of the switches can be varied to produce different tube configurations. For example, actuation of switch 152 by cam 140 can be varied with respect to the actuation of the other two switches to vary the location of the auxiliary lumen in the extrudate. In the system of FIG. 7, the pressure at the left or tip end of the auxiliary lumen forming pin 68 is reduced from the value necessary to form the auxiliary lumen at preselected portions of the tubular extrudate. Preferably, and as shown in the drawing, the pressure in the melt 52 at the top of pin 68 is reduced to a negative value to fully eliminate the auxiliary lumen. However, a reduction in the pressure at that point will tend to reduce the size of the lumen and in some cases even completely close it. In some cases, the use of a small lumen or one almost eliminated is satisfactory and will not necessarily produce a leakage path.

In forming a tube from the tubular extrudate, for example, such as medical tube 32 in FIG. 4, the extrudate is severed through at the enlargement of bubble 102 so that the end portion is conical or increases radially outwardly toward the proximal end of the severed tube, as seen at 36 in FIG. 4. The distal end may be severed through at the constant diameter portion 100 (FIG. 7) and then the end of the lumen closed, such as by remelting the end in a mold to form a closed integral tip indicated at 38 in FIG. 4. Before the end 38 is formed, the inner wall of the tube may be nicked or cut to connect the interior of the main lumen 40 with the auxiliary lumen 42. Also, the openings 43 may be thereafter cut in the side wall in appropriate locations. Such tubes as 32 may be continously cut from continuous extrusion of extrudate having straight portions 100 and bubbles 102. The main lumen being enlarged and the auxiliary lumen being reduced or eliminated at preselected portions of the extrudate.

In FIG. 8, apparatus for producing tubular extrudate in accordance with a modified method is illustrated. A die 200 is shown having a die cavity 202 connected to receive molten plastic 204 from an extruder 206. A die forming member 208 in the cavity is provided with a main lumen forming pin 210 and an auxiliary lumen forming pin 212. Tubular extrudate 214 issues from the die orifice 216 and has a main lumen 218 and auxiliary lumen 220 in preselected portions of the tubing.

The main lumen pin 210 has its bore connected to a controlled air pressure source 222 which may include air supply valves and which is controlled by a programmer 224 that may be of the electronic type or of the mechanical type such as illustrated in FIG. 7.

The auxiliary lumen forming pin 212 is axially movable and has its lumen connected in fluid communication to the controlled air pressure source 222 by means of a fluid coupler 226 and a flexible tube 228 so as to receive a supply of air from the source 222. The coupling element 226 is mechanically connected by a rod 230 to a piston 231 of an air cylinder to actuator 232 for moving the pin 212 axially.

A solenoid actuated air supply valve 234 has its inlet port connected to an air pressure regulator 236 which is supplied air from a pressurized air source 238. Valve 234 has a slide valve member 240 spring biased rightwardly so that in the position shown, air is supplied to an outlet conduit 242 which connects with the right side of the air cylinder piston 231 to maintain the auxiliary lumen pin 212 in the position shown in the drawing. The air supply valve 234 has a solenoid coil 244 which, when energized, shifts the slide valve member 240 leftwardly to close the outlet conduit 242 from the supply of air and connect the supply of air from regulator 236 to a second outlet conduit 246 which is connected to the left side of the cylinder piston 231 to effect rightward movement from the piston rod 230 and, therefore, rightward movement of the auxiliary lumen forming pin 212. Coil 244 has one side grounded and the other side connected by a lead 248 to the programmer 224 which controls the energization of the coil.

The programmer may also operate an extrudate takeoff drive mechanism (not shown) such as of the type illustrated in FIG. 7 at 124. The programmer 224 synchronously controls the air supplied to the main and auxiliary lumen forming pins 210 and 212 as well as controlling the axial movement of the pin 212, and where desired, the withdrawal rate of the tubular extrudate 214.

In operation, with the valve 234 and cylinder 232 in the operating conditions illustrated, air is supplied to the right hand side of the actuating cylinder 231 by the valve 234 to maintain the auxiliary lumen forming pin 212 in the position shown, that is, with the left end at the orifice 216. The programmer also supplies a controlled or desired amount of air to both the main lumen and auxiliary forming pins 210 and 212 so that the extrudate 216 produces a main lumen 218 and an auxiliary lumen 220 within the wall of the extrudate as illustrated in FIG. 8. At a preselected time during the extrusion of tubular extrudate 214, for example, during the forming of a bubble, the programmer provides a signal to the controlled air pressure source to increase the amount of air or air pressure to the main lumen forming pin 210 and may reduce or maintain the air pressure supplied to the auxiliary lumen pin 212, and energize solenoid coil 244 to effect a shifting of the slide valve 240 leftwardly. This supplies air through conduit 246 to the left side of the actuator 231 to shift the auxiliary lumen forming pin 212 axially rightwardly. This movement of the pin 212 away from the die orifice 216 allows the molten plastic 204 to flow together closing the previously formed auxiliary lumen 220 in the tubular extrudate. Thus, for example, the lumen 220 may be terminated before or during the forming of a bubble in the extrudate. The programmer, depending on a particular program, may after the bubble is formed, de-energize coil 244 cuasing the valve 240 to move rightwardly to supply air to the right-hand side of actuator 231 to thereby effect return leftward movement of the pin 212 to again effect the formation of auxiliary lumen 220. The programmer may then cause the controlled air pressure source 222 to reduce the amount of air pressure supplied to the main lumen forming pin 210 to thereby again produce a relatively small main lumen 218 or straight portion of tubing. In some cases, the axial movement of the end of pin 212 rightwardly away from the left end of the die or orifice 216 without changing the amount of air normally supplied to the pin 212, may simply effect a desired reduction or elimination of the auxiliary lumen in the tubular extrudate. Movement of the pin 212 as well as varying the gas or air supplied thereto can be used to obtain desired effects.

Another feature of the embodiment illustrated in FIG. 8 is that the auxiliary lumen forming pin 212 may be rotated on its own axis so that the auxiliary lumen formed in the tubular extrudate may be varied in location radially between the inner and outer walls of the tube. FIG. 9 illustrates extrudate 214 with the auxiliary lumen 220 closer to the outer surface while FIG. 10 shows the lumen 220 closer to the main lumen. This is accomplished by constructing the pin 212, as best seen in FIG. 11, such that it has a straight end portion 250 which is in spaced parallel relation with pin 210, an angularly extending portion 252 and a straight portion 254 which is radially inwardly from portion 250 and which extends through the forming member 208. It will be apparent that by rotating pin 212 on its own axis, the end portion 250 of the pin will move radially toward and away from the pin 210, and its rotation will cause the auxiliary lumen in the tubular extrudate to also vary radially with respect to the main lumen. In this way, the auxiliary lumen may be readily adjusted accurately to a desired location. FIG. 11 illustrates the auxiliary lumen pin 212 retracted from the orifice 210 so as to eliminate any auxiliary lumen in the extrudate. It is also shown rotated from its position shown in FIG. 8. Movement of the pin 212 in a direction to move its left end away from the left end of the die and orifice 216, reduces the gas pressure at the orifice 216 even if the air supplied to the lumen of pin 212 remains the same. Thus, gas pressure at the orifice can be reduced to reduce or eliminate the auxiliary lumen in the extrudate by merely moving the pin 212 or by reducing the pressure of air supplied to the lumen of the pin 212. Movement of the pin 212 rightwardly from the orifice 216 reduces die swell that occurs as the take-off rate of the extrudate is reduced. Thus, by controlling the movement of the pin 212 as desired or programmed, the size of the auxiliary lumen can be varied in a desired manner or in predetermined portions of the extrudate.

FIG. 12 illustrates a plastic medical tube of modified form which may be made by either of the methods described in connection with the apparatus of FIG. 7 or 8. The extrudate, such as extrudate 99 (FIG. 7), is severed near the start of the bubble 102 so that the completed tube 260 provides an end portion which may be inserted into a female fluid coupling element, such as element 262 (FIG. 12). The element 262 may, in turn, be coupled to another tube such as tube 264 shown in phantom. The tube 260, in this case, is shown with an auxiliary lumen 266 in the substantially straight portion and with it extending only slightly into the bubble. The lumen being eliminated in the portion of the bubble or tube which is inserted into the coupling element 262 to thereby preclude the possibility of a leak.

Thus, by reducing the air or gas pressure in the extrudate at the orifice 216 or left end of the die by moving the pin 212 rightwardly away from the orifice or by reducing the pressure of air supplied to the lumen of pin 212, the auxiliary lumen 220 can be reduced or eliminated.

Die swell which typically causes the auxiliary lumen to increase in size as the take-off speed of the extrudate is reduced, can be reduced by moving the auxiliary lumen forming pin rightwardly away from the die orifice. Thus, by moving the forming pin axially, the size of the auxiliary lumen can be readily varied to obtain a desired lumen size.

While elimination of the auxiliary lumen in enlarged portions of tubular extrudate has been illustrated herein, tubes having various configurations, such as those having constant inner and outer diameters, can be formed with preselected portions free of auxiliary lumens and for purposes other than avoiding leakage paths between associated coupling elements and the tube. For example, the auxiliary lumen may be eliminated in a portion of a tube for the purpose of preventing gas or liquid from passing beyond selected portions of the auxiliary lumen.

As various changes could be made in the above described apparatus, methods and tubes without departing from the scope of the invention, it is intended that all matter contained in the above description and shown in the accompanying drawings be interpreted as illustrative and not in a limiting sense.

What is claimed is:

1. A method of making a plastic tube having a main body portion and an integral connector portion adapted for connection with a fluid coupling element comprising the steps of extruding molten plastic material through a die having a die orifice, a main lumen forming member for producing tubular extrudate with a main lumen issuing from the die orifice, and a hollow auxiliary lumen forming pin with an end adjacent the die orifice for producing a longitudinally extending auxiliary lumen in the sidewall of the extrudate, supplying gas to said forming pin to provide a predetermined gas pressure in the sidewall of the extrudate adjacent the die orifice for producing an auxiliary lumen in a predetermined portion of the extrudate having a diameter less than the thickness of the sidewall to produce said main body portion, reducing the gas pressure in the sidewall of the extrudate adjacent the die orifice during the extrusion of a selected portion of the extrudate to limit the size of or eliminate the auxiliary lumen in said selected portion to produce said connector portion, and severing the extrudate to produce a tube having said main body and connector portions therein with the main lumen extending in both of said main body and connector portions.

2. the method of claim 1 wherein the step of reducing the gas pressure includes the step of reducing the gas pressure supplied to said forming pin.

3. The method of claim 2 wherein the gas pressure supplied to siad forming pin is reduced to a value which effects substantial elimination of the auxiliary lumen in said selected portion.

4. The method of claim 1 wherein the step of reducing the gas pressure includes moving said forming pin inwardly of the die away from the die orifice.

5. The method of claim 1 further including the step of supplying gas under pressure to said main lumen forming member and changing the pressure supplied at programmed intervals during the extrusion of the extrudate to produce said body portion and a plurality of said connector portions with said connector portions having greater inner and outer diameters than those of said main body portion.

6. The method of claim 5 wherein the step of reducing the gas pressure in the side wall of the extrudate adjacent the die orifice includes reducing the gas pressure supplied to said forming pin to substantially eliminate the auxiliary lumen in each of said selected portions of the extrudate.

7. The method of claim 6 wherein the step of severing the extrudate includes cutting the extrudate through one of said selected portions 8. The method of claim 6 wherein the step of reducing the gas pressure is correlated with said programmed intervals.

9. The method of claim 8 wherein the forming of each of said connector portions includes withdrawing the extrudate from the die at a preselected rate, and the step of forming said predetermined portion includes a withdrawing the extrudate at a higher rate.

10. The method of claim 1 wherein the step of reducing the gas pressure includes the step of applying a negative pressure to said forming pin to eliminate the auxiliary lumen in said selected portion of the extrudate.

11. The method of claim 1 wherein the molten plastic is extruded through the die so that the main lumen extends to the severed end of the tube.

12. The method of claim 1 wherein the extrudate is severed at a location where the auxiliary lumen is reduced or eliminated but which contains the main lumen.

13. The method of claim 1 wherein the extrudate is substantially circular in cross-section substantially throughout its length.

14. A method of making a plastic tube comprising the steps of extruding plastic material through a die having a die orifice, a main lumen forming member for producing tubular extrudate with a main lumen, and a hollow auxiliary lumen forming pin with an end adjacent the die orifice, supplying gas to said forming pin to provide a predetermined gas pressure in the side wall of the extrudate adjacent the die orifice for producing an auxiliary lumen in a predetermined portion of the side wall of the extrudate, reducing the gas pressure in the side wall of the extrudate adjacent the die orifice during the extrusion of a selected portion of the extrudate to reduce the size of or eliminate the auxiliary lumen in the selected portion of the extrudate, and severing the extrudate to produce a tube having said predetermined and selected portions therein, said forming pin including a tubular member having a first portion rotatable on its own longitudinal axis, and an end portion displaced from said axis so that upon rotation of said first portion on said axis the distance between said end portion and said main lumen forming member varies, and rotating said forming pin to adjust the radial position of said auxiliary lumen in said predetermined portion of the extrudate.

15. The method of making a plastic tube having a main lumen and an auxiliary lumen in the side wall of the tube comprising extruding molten plastic through a die having a die orifice from which the extrudate issues, a main pin having an end adjacent the orifice for producing tubular extrudate having a main lumen, and an auxiliary pin having a movalbe end portion adjacent the orifice for producing an auxiliary lumen of smaller diameter than the thickness of the side wall of the extrudate and which extends longitudinally of the extrudate, the auxiliary pin having a rotatable portion connected to said end portion and having an axis displaced from the axis of the end portion, and adjustably rotating the rotatable portion to adjust the radial position of the end portion and the position of the auxiliary lumen in the side wall of the extrudate.

16. A method of making a plastic tube comprising the steps of extruding molten plastic material through a die having a die orifice and a main lumen forming member for producing tubular extrudate issuing from the die orifice with a main lumen, controlling the flow of the extrudate through the die to produce a first portion with predetermined inner and outer diameters and an integral second portion with inner and outer diameters greater than those of said first portion and having tapering leading and trailing portions, and with the main lumen extending in both of the first and second portions, said die further having a hollow auxiliary lumen forming pin with an end adjacent the die orifice for producing a longitudinally extending auxiliary lumen in the sidewall of the extrudate, supplying gas to said forming pin to provide a predetermined gas pressure in the extrudate adjacent the die orifice for producing an auxiliary lumen in said first portion of the extrudate having a diameter less than the thickness of the sidewall, reducing the gas pressure within the sidewall of the extrudate adjacent the die orifice during the extrusion of said second portion of the extrudate to substantially eliminate or limit the size of the auxiliary lumen in said second portion, and severing the extrudate through said second portion to produce a tube having said first portion, and a part of said second portion at the severed end of the tube adapted for frictional sealing connection with a fluid coupling device adapted for fluid communication with the main lumen, and with the main lumen extending to the severed end of the tube.

17. The method of claim 16 wherein the step of reducing the gas pressure includes the step of reducing the gas pressure supplied to said forming pin.

18. The method of claim 16 wherein the step of reducing the gas pressure includes moving said forming pin inwardly of the die away from the die orifice.

* * * * *